(12) United States Patent
York et al.

(10) Patent No.: US 9,199,907 B2
(45) Date of Patent: Dec. 1, 2015

(54) PROCESS FOR THE PRODUCTION OF ETHYLENICALLY UNSATURATED CARBOXYLIC ACIDS FOR ESTERS AND A CATALYST THEREFOR

(71) Applicant: Lucite International UK Limited, Southampton (GB)

(72) Inventors: Ian Andrew York, Wilton (GB); Sabina Ziemian, Wilton (GB)

(73) Assignee: Lucite International UK Limited (GB)

(*) Notice: Subject to any disclaimer, the term of this patent is extended or adjusted under 35 U.S.C. 154(b) by 0 days.

(21) Appl. No.: 14/371,250

(22) PCT Filed: Jan. 14, 2013

(86) PCT No.: PCT/GB2013/050062
§ 371 (c)(1),
(2) Date: Jul. 9, 2014

(87) PCT Pub. No.: WO2013/104924
PCT Pub. Date: Jul. 18, 2013

(65) Prior Publication Data
US 2014/0364645 A1    Dec. 11, 2014

(30) Foreign Application Priority Data

Jan. 13, 2012   (GB) .................................. 1200551.8

(51) Int. Cl.

| | | |
|---|---|---|
| C07C 51/377 | (2006.01) |
| C07C 67/317 | (2006.01) |
| B01J 27/18 | (2006.01) |
| B01J 37/03 | (2006.01) |
| B01J 27/10 | (2006.01) |
| B01J 27/12 | (2006.01) |
| B01J 35/00 | (2006.01) |
| B01J 35/02 | (2006.01) |
| B01J 35/10 | (2006.01) |
| C07C 67/343 | (2006.01) |
| C07C 51/353 | (2006.01) |

(52) U.S. Cl.
CPC ............... *C07C 51/377* (2013.01); *B01J 27/10* (2013.01); *B01J 27/12* (2013.01); *B01J 27/1806* (2013.01); *B01J 35/002* (2013.01); *B01J 35/026* (2013.01); *B01J 35/1009* (2013.01); *B01J 35/1014* (2013.01); *B01J 37/038* (2013.01); *C07C 51/353* (2013.01); *C07C 67/317* (2013.01); *C07C 67/343* (2013.01); *C07C 2527/18* (2013.01)

(58) Field of Classification Search
CPC   C07C 2527/18; C07C 67/317; C07C 51/377; B01J 27/1806
See application file for complete search history.

(56) References Cited

U.S. PATENT DOCUMENTS 2,859,240 A  * 11/1958  Holmen .................... 560/212
4,118,588 A    10/1978  Fouquet et al.

FOREIGN PATENT DOCUMENTS

| GB | 865 379 A | 4/1961 |
|---|---|---|
| WO | WO2012063044 A1 * | 4/2011 |
| WO | 2012 001395 A1 | 1/2012 |

OTHER PUBLICATIONS

International Search Report from European Patent Office for International Patent Application No. PCT/GB2013/050062, (2013).

* cited by examiner

*Primary Examiner* — Yong Chu
(74) *Attorney, Agent, or Firm* — Shumaker, Loop & Kendrick, LLP

(57) ABSTRACT

A method of producing an ethylenically unsaturated, typically, an α, β ethylenically unsaturated carboxylic acid or ester is described. The method comprises the steps of contacting formaldehyde, or a source of formaldehyde, with a carboxylic acid or ester in the presence of a catalyst and optionally in the presence of an alcohol. The catalyst comprises barium phosphate leaf or plate shaped/like crystals, or a source thereof. A catalyst system is also described. The catalyst system comprises a crystalline barium phosphate catalyst and optionally a catalyst support.

16 Claims, 9 Drawing Sheets

PROCESS FOR THE PRODUCTION OF ETHYLENICALLY UNSATURATED CARBOXYLIC ACIDS FOR ESTERS AND A CATALYST THEREFOR

CROSS-REFERENCE TO RELATED APPLICATION

This U.S. National Stage Application claims priority from PCT/GB2013/050062 filed Jan. 14, 2013, which claims priority from GB 1200551.8 filed Jan. 13, 2012, the entirety of which are incorporated herein by reference.

TECHNICAL FIELD AND BACKGROUND OF THE INVENTION

The present invention relates to a process for the production of ethylenically unsaturated carboxylic acids or esters, particularly α, β unsaturated carboxylic acids or esters, more particularly acrylic acids or esters such as (alk)acrylic acids or alkyl (alk)acrylates particularly (meth)acrylic acid or alkyl (meth)acrylates such as methyl methacrylate by the condensation of carboxylic acid or esters with formaldehyde or a source thereof such as dimethoxymethane in the presence of catalysts, in particular, by the condensation of propionic acid or alkyl esters thereof with formaldehyde or a source thereof in the presence of such a catalyst system. The invention is therefore particularly relevant to the production of methacrylic acid (MAA) and methyl methacrylate (MMA).

As mentioned above, such unsaturated acids or esters may be made by the reaction of a carboxylic acid or ester and suitable carboxylic acids or esters are alkanoic acids (or ester) of the formula $R^3$—$CH_2$—$COOR^4$, where $R^3$ and $R^4$ are each, independently, a suitable substituent known in the art of acrylic compounds such as hydrogen or an alkyl group, especially a lower alkyl group containing, for example, 1-4 carbon atoms. Thus, for instance, methacrylic acid or alkyl esters thereof, especially methyl methacrylate, may be made by the catalytic reaction of propionic acid, or the corresponding alkyl ester, e. g. methyl propionate, with formaldehyde as a methylene source in accordance with the reaction sequence 1.

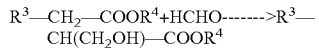

and

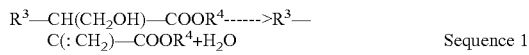

Sequence 1

An example of reaction sequence 1 is reaction sequence 2

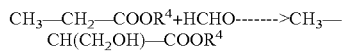

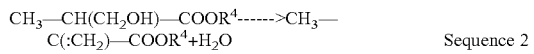

Sequence 2

A further reaction sequence is one which uses an acetal

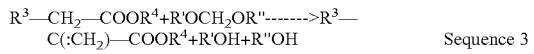

Sequence 3

A theoretical example of reaction sequence 3 is reaction sequence 4 which uses dimethoxymethane

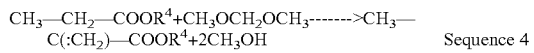

Sequence 4

The use of dimethoxymethane thus theoretically gives an anhydrous system which avoids the difficulty of subsequent water separation and/or subsequent product hydrolysis. In addition, the use of dimethoxymethane avoids the use of free formaldehyde but nevertheless acts in a general sense as a source of formaldehyde. The absence of water and free formaldehyde could greatly simplify the separation of MMA from the product stream.

However, in practice, Sequence 4 is problematic because methanol dehydrates to dimethyl ether and water. In addition, dimethoxymethane decomposes under catalytic conditions to dimethylether and formaldehyde. Any water formed in these reactions can hydrolyse the ester feedstock or product to its corresponding acid which may be undesirable.

U.S. Pat. No. 4,560,790 describes the production of α, β unsaturated carboxylic acids and esters by the condensation of methylal(dimethoxymethane) with a carboxylic acid or ester using a catalyst of general formula $M^1/M^2/P/O$ wherein $M^1$ is a group IIIb metal, preferably aluminium, and $M^2$ is a group IVb metal, preferably silicon.

As mentioned above, a known production method for MMA is the catalytic conversion of methyl propionate (MEP) to MMA using formaldehyde. A known catalyst for this is a caesium catalyst on a support, for instance, silica.

U.S. Pat. No. 4,118,588 discloses the production of methyl methacrylate and methacrylic acid by reacting propionic acid or methyl propionate with dimethoxymethane in the presence of catalysts based on the phosphates and/or silicates of magnesium, calcium, aluminium, zirconium, thorium and/or titanium and also in the presence of 0 to 0.5 moles of water per mole of the acetal. The preferred phosphates are aluminium, zirconium, thorium and titanium. The catalysts generally include an oxide modifier to improve the catalytic activity. Magnesium phosphate is not exemplified and calcium phosphate is not exemplified alone but one example with an oxide modifier is provided. The results are poor compared with the other phosphates, particularly aluminium.

It is known from GB865379 that group II metal phosphates, in particular barium phosphates, can exist in crystallographic form of rhombic or cubic crystals and that these are active in catalysing the production of acrylic acid or lower alkyl esters from chloropropionic acid by direct catalytic vapour phase dehydrochlorination.

SUMMARY OF THE INVENTION

The present inventors have now discovered that barium phosphates form plate or leaf like crystals when existing as barium orthophosphate, barium hydrogen phosphate or barium pyrophosphate.

The current inventors have also found that these plate/leaf crystal habits of barium phosphate provide a high level of selectivity in the condensation of methylene sources such as formaldehyde with a carboxylic acid or alkyl ester such as methyl propionate.

Therefore surprisingly, it has now been found that barium metal phosphates having plate or leaf shaped crystals are remarkably effective catalysts for the production of α, β ethylenically unsaturated carboxylic acid or esters by condensation of the corresponding acid or ester with a methylene source such as formaldehyde or dimethoxymethane providing high selectivity and low dimethylether (DME) production. In particular, the catalysts are particularly suited to the production of α, β ethylenically unsaturated carboxylic esters because they produce little water in such reactions thus avoiding undesirable side reactions.

DETAILED DESCRIPTION OF THE INVENTION

According to a first aspect of the present invention there is provided a method of producing an ethylenically unsaturated carboxylic acid or ester, preferably an α, β ethylenically unsaturated carboxylic acid or ester, comprising the steps of contacting formaldehyde or a suitable source thereof with a carboxylic acid or ester in the presence of a catalyst and optionally in the presence of an alcohol, wherein the catalyst comprises barium phosphate leaf or plate shaped crystals, or a suitable source thereof.

By the term "a suitable source thereof" in relation to the phosphate crystals is meant that the crystals may be formed in situ from the phosphate source under reaction conditions. By leaf or plate shaped/like crystals is generally understood a plate/leaf like habit.

Suitable examples of phosphates in accordance with the present invention include pyrophosphate, orthophosphate ($PO_4^{3-}$), hydrogenphosphate and mixtures thereof, more preferably, orthophosphate, pyrophosphate and mixtures thereof.

Particularly preferred catalysts are barium pyrophosphate and barium orthophosphate ($PO_4^{3-}$) which both form leaf or plate like crystals.

Preferably, the catalyst is at least 50% w/w barium phosphate, more preferably, at least 70% barium phosphate, most preferably, at least 80% barium phosphate. The barium phosphate preferably has a significant crystalline barium phosphate fraction but may also include a balance of amorphous material. Known crystalline habits of the barium phosphates are rod/needle like or plate/leaf like. The inventors have surprisingly found that crystalline barium phosphates with at least some plate/leaf like crystals have surprisingly high product selectivity to the α,β ethylenically unsaturated carboxylic acid or ester in the present invention, particularly over the alternative rod/needle like crystal habit.

The crystal habit of the barium phosphate may be determined by techniques known to those skilled in the art, for example by transmission electron microscopy (TEM) or scanning electron microscopy (SEM). Preferably, plate/leaf like crystals are on average the dominant crystal habit numerically in the phosphate. Plate/leaf like includes at least those habits described as blade, platy or tabular but as wider plates are preferred, they more typically encompass, platy or tabular, and as thinner plates are also preferred they most typically encompass a platy habit. Preferably, plate/leaf like crystals are on average the dominant crystal habit by amount of average TEM image area covered in the phosphate. By dominant is meant that the crystalline habit is the largest group of crystals. However, it is not necessary for the plate/leaf like habit to be the dominant crystal habit for the invention to be effective. Even a barium phosphate with a minority of the crystals in the plate or leaf like habit will be still effective as a catalyst. Accordingly, the barium phosphate crystals having the plate or leaf like habit or suitable source thereof need only be present or become present at a level that is effective to catalyse the reaction with sufficient selectivity such as those selectivities set out below.

Preferably, the selectivity of the reaction to ethylenically unsaturated carboxylic acid or ester, preferably α, β ethylenically unsaturated carboxylic acid or ester product, especially (alk)acrylic acid or alkyl (alk)acrylate product is at least 40 mole %, more preferably, at least 60 mole %, most preferably, at least 70 mole %, especially, at least 80 or 90 mole %, more especially, 94 mole %.

Advantageously, the inventors have found that the plate/leaf like habit of barium phosphates can achieve selectivity up to above 95 mole % and can preferably be maintained at least above 90 mole %.

Typical selectivities as set out above are in the range 45-100 mole %, more preferably, 65-100 mole %, most preferably, 75-100 mole %, especially, 85 or 90-100 mole %. The mole % may be determined by gas chromatography. Selectivity based on mole % refers to total product converted from the starting carboxylic acid or ester. For example, if 100 g methyl propionate reacts to produce 90 g of methyl propionate and 10 g of propionate derived product of which 9 g is methyl methacrylate then the reaction is 90% selective to methyl methacrylate by weight which may be converted to mole % selectivity using the relevant molecular weights to determine moles methyl propionate converted to product and moles of methyl methacrylate produced and calculating the mole % of methyl methacrylate therefrom. Similarly, the same analysis can be carried out for other components such as methacrylic acid. A suitable gas chromatography device is a Shimadzu GC GC2010, equipped with a RTX1701 column (supplied by Thames Restek UK Ltd) & a Flame Ionization Detector (FID).

Reactor feed compositions and samples of the condensed flow exiting the catalytic reactor may all be analysed by gas chromatography. A suitable device is the Shimadzu GC detailed above. For each analysis, the resultant chromatograph may be processed using Shimadzu's "GC Solutions" software to obtain peak areas for individual components. The FID response factors for the individual components obtained using standards are applied to convert peak areas, first into wt %, and then into mole %, of detectable material in the sample.

Water content in the product of the catalytic reaction may be measured by a Karl-Fischer titration (Mettler Toledo DL38, with a probe DM143-SC, Hydranal Working Medium K and Composite K).

Preferably, the plate-like shaped crystals are in a sufficiently open arrangement to provide access to their surfaces to effect sufficient catalysis. In a congealed mass of crystals the surface area of the plate like crystals available for catalysis may be reduced thus reducing although not removing catalytic effectiveness. Accordingly, the barium phosphate crystals of the invention are preferably, substantially non-agglomerated or non-congealed.

Preferably, at least 10% mol/mol of the total barium phosphate in the catalyst is in a crystalline form, more preferably, at least 30% mol/mol, most preferably, at least 50% mol/mol. Typically, amorphous material (or fraction of crystalline phase) can be estimated based on XRD results from the equation:

$$Xc=(1-v112/300)/I300$$

where I300 is the intensity of the (300) diffraction peak and _v112/300 is the intensity of the hollow between the (112) and (300) diffraction peaks; Xc is the degree of crystallinity.

Generally, the average crystal size (the size in the largest dimension) of the barium phosphate crystals is in the range 0.002-50 μm. In particular, the plates are generally, on average, 0.002-2 μm thick, more typically, 0.01-1.0 μm, most preferably, 0.05-0.5 μm thick and 0.002-20 μm, more preferably, 0.1-10 μm, most preferably, 0.5-2 μm in length and preferably have the aspect ratios defined herein. Accordingly, in this context, the shape of the crystals of the invention may be termed micro-plates.

Advantageously, the use of barium phosphate catalysts in the process of the invention also results in surprisingly low levels of dimethyl ether in the product stream whether the formaldehydic component of the vaporised reactor feed composition is based on formaldehyde or dimethoxymethane.

It has also been found that the catalyst of the invention maintains effectiveness when the surface layer of the crystals is varied around the optimum Ba:P molar ratio for the orthophosphate i.e. 1.5. By surface ratio herein we refer to the ratio as determined by X-ray photoelectron spectroscopy (XPS).

The general formula of barium pyrophosphate in accordance with the invention may be given as formula I $$Ba_2P_2O_7 \qquad \qquad I$$

The general formula of barium orthophosphate in accordance with the invention may be given as formula II $$Ba_3(PO_4)_2 \qquad \qquad II$$

The general formula of barium hydrogenphosphate in accordance with the invention may be given as formula III $$Ba(HPO_4) \qquad \qquad III$$

As will be appreciated, the Ba:P mole ratio in pure barium phosphate can be varied for example around the optimum ratio of 3:2 for barium orthophosphate or 1:1 for the pyrophosphate or hydrogenphosphate. It is possible for the Ba:P mole ratio in the barium phosphate leaf or plate shaped crystals to vary between 0.5-2.0 but typical surface Ba:P ranges for the orthophosphate are 1.0-1.8, especially, 1.1-1.7, more especially, 1.2-1.6 as determined by XPS whereas bulk Ba:P mole ratios vary between 1.1-1.5, more typically, 1.2-1.4, as determined by X-Ray Fluorescence Spectrometry (XRF). On the other hand typical surface Ba:P ranges for the pyrophosphate and hydrogen phosphate are 0.6-1.4, especially, 0.7-1.3, more especially, 0.8-1.25 as determined by XPS whereas bulk Ba:P mole ratios vary between 0.6-1.1, more typically, 0.8-1.0 as determined by X-Ray Fluorescence Spectrometry (XRF). A suitable instrument for determining surface Ba:P ratios by XPS is a Kratos "Axis Ultra" X-ray Photoelectron Spectrometer. A suitable instrument for determining bulk Ba:P ratios by XRF is an Oxford Instruments X-Supreme 8000 which is based on Energy Dispersive X Ray Fluorescence measurements (EDXRF).

Varying Ba:P ratios in the final crystals can be achieved by varying precursor Ba:P ratios and/or in the case of a wet production method, the solution pH and/or solution temperatures.

Generally, production of the plate or leaf like shaped crystals of the invention is achieved by appropriate methods known to the skilled person as already set out above.

A preferred production method for production of barium orthophosphate plate like crystals according to the invention uses a simple wet method of combining barium nitrate, chloride or hydroxide and diammonium hydrogenphosphate as barium and phosphorus precursors respectively in aqueous solution to form a precipitate. Continuous stirring may maintain the product in suspension. After ageing, the product is preferably dried at 100 to 140° C. and calcined at 200-600° C., more preferably 300-500° C., most preferably 350-450° C.

The catalyst wet synthesis solution temperature in the above or other methods may be from 0-150° C., typically, from 25-130° C., more typically, from 70-110° C.

Typically, the catalyst synthesis pH in the above or other suitable methods may be from 7-14, more typically, from 9-13.5, most typically, from 10-13.2.

Still further techniques include thermolysis, in a furnace at >500° C. For preparation by thermolysis, a physical mixture of thermally unstable barium and phosphorus compounds (e.g. barium nitrate, barium hydroxide, barium carbonate, diammonium hydrogen phosphate, phosphoric acid) is heated in a flow of air at temperatures from 500-2000° C.

The crystalline habit of the barium orthophosphate may be determined by TEM or XRD. Preferably, it is determined by TEM inspection and optionally confirmed by XRD. The absence or presence of crystallinity is preferably determined by XRD. A suitable instrument for XRD analysis is the Siemens Bruker D5000 Diffractometer D6. A suitable instrument for TEM analysis is a Philips CM12 Transmission Electron Microscope.

Crystalline barium orthophosphate has characteristic XRD peaks at angle 2 Theta: 28.0, 31.9, 38.5 and 47.1. Crystalline barium pyrophosphate has characteristic XRD peaks at 24.9, 27.2, 31.9, 42.4 and 46.8.

According to a second aspect of the present invention there is provided a catalyst system comprising a crystalline barium phosphate catalyst and optionally a catalyst support wherein the barium phosphate is in the form of leaf or plate shaped crystals, or a suitable source thereof.

Advantageously, the leaf/plate like shaped crystals provide a surprisingly high selectivity for an ethylenically unsaturated acid or ester product in a catalysed reaction according to the first aspect of the present invention.

The references to a leaf or plate like shaped crystal of barium phosphates is self explanatory to the skilled person but in case of doubt may be taken to indicate a crystal with preferential growth in two key dimensions (the z and the y axis) and a substantially lower growth in a third dimension (the x axis). More specifically, a leaf/plate like shaped crystal has a length, a width and a thickness. The z and y axes can be defined interchangeably as the length and width. The x axis can be defined as the thickness. The width to length ratio may be unequal. Alternatively the width : length ratio may be substantially equal, for example it may be between 1:4 and 4:1, more typically between 1:3 and 3:1, most typically, between 1:2 and 2:1, especially, 2:3 and 3:2 and most especially between 3:4 and 4:3. In any case, the length and width will always be far greater than the thickness; wherein an aspect ratio of the length and/or width (z and y axes): thickness (x axis) >5, typically, >10, more typically, >20, especially, >40.

The leaf/plate like shape as defined in the present invention is intended to cover any crystal that has the above dimensions and therefore has the appearance macroscopically or microscopically of being in a thin planar habit with likeness to a plate or a leaf. Therefore, plate or leaf like shape includes any of the known crystal forms capable of a plate of leaf like appearance. However, it is believed that a particular crystal structure and form of the barium phosphate of the invention may cause it to produce the characteristic crystalline habit of the invention and that the presence of this habit is indicative of a particular crystal structure and form. For the avoidance of doubt, habit herein means the external appearance of a crystal. In this respect, it will be appreciated that not all crystals will be perfectly formed and that, in any case, the crystals are likely to agglomerate. Nevertheless, the crystal habit should still be discernible by simple inspection, by TEM or SEM, for instance.

Optionally, the catalytic performance and/or the level of plate/leaf like crystals can be modified by changes applied to the catalyst synthesis conditions such as pH, temperature, pressure, Ba:P ratio and through doping with other elements, especially metals.

The pH and temperature of crystal synthesis reaction have been outlined above. The pressure of reaction is also not critical and the catalyst can be prepared at reduced or high pressure. Typically, however, the catalyst is synthesised at or around atmospheric pressure.

Suitable doping elements may be present in the catalyst at a level up to 20 mol % of the metal M. Suitable doping metal cations are Cs, K, Rb, Na, Li, Zn, Ti, Si, Ln, Ce, Eu, Mg, Pb, Cd, Ag, Co, Cu, Ni, Sn, Ge, Hf and Zr. Preferred dopants are group I alkali metals and group II alkaline earth metals from the above list, more preferably, group I metals, especially Cs.

Suitably the doping element is not present in the catalyst above the level of 50 mol % of the metal.

The doping cations may replace Barium in the above formulas.

Suitable doping anions may be present at a level of up to 20 mol % phosphate. Suitable doping anions are chloride and fluoride. These may be assumed to partially replace the phosphate or phosphorus in the formulas herein as appropriate.

Preferably, the carboxylic acid or ester reactant of the present invention is of formula $R^3$—$CH_2$—$COOR^4$ wherein $R^4$ is either hydrogen or an alkyl group and $R^3$ is either hydrogen, an alkyl or aryl group.

Formaldehyde and Sources Thereof

By the term "a suitable source thereof" in relation to formaldehyde of the first aspect of the present invention is meant that the free formaldehyde may either form in situ from the source under reaction conditions or that the source may act as the equivalent of free formaldehyde under reaction conditions, for example it may form the same reactive intermediate as formaldehyde so that the equivalent reaction takes place.

A suitable source of formaldehyde may be a compound of formula I

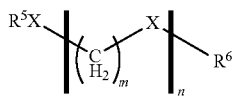

wherein $R^5$ and $R^6$ are independently selected from $C_1$-$C_{12}$ hydrocarbons or H, X is O, n is an integer from 1 to 100, and m is 1.

Preferably, $R^5$ and $R^6$ are independently selected from $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H. Preferably, n is an integer from 1 to 10, more preferably 1 to 5, especially, 1-3.

However, other sources of formaldehyde may be used including trioxane.

Therefore, a suitable source of formaldehyde includes any equilibrium composition which may provide a source of formaldehyde. Examples of such include but are not restricted to dimethoxymethane, trioxane, polyoxymethylenes $R^1$—O—($CH_2$—O)$_i$—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propionate.

Typically, the polyoxymethylenes are higher formals or hemiformals of formaldehyde and methanol $CH_3$—O—($CH_2$—O)$_i$—$CH_3$ ("formal-i") or $CH_3$—O—($CH_2$—O)$_i$—H ("hemiformal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—(CH2-O—)$_i R^{32}$, where $R^{31}$ and $R^{32}$ may be the same or different groups and at least one is selected from a $C_1$-$C_{10}$ alkyl group, for instance $R^{31}$=isobutyl and $R^{32}$=methyl.

Preferably, the suitable source of formaldehyde is selected from dimethoxymethane, higher hemiformals of formaldehyde and methanol, $CH_3$—O—($CH_2$—O)$_i$—H where i=2, formalin or a mixture comprising formaldehyde, methanol and methyl propionate.

It is particularly advantageous that dimethoxymethane can be used as a source of formaldehyde in the present invention. Advantageously, this provides the possibility of reacting dimethoxymethane with methyl propionate to form MMA and methanol without the production of water. This provides a potentially anhydrous system i.e. a system with reduced water side reactions and separation requirements than one using other sources of formaldehyde which contain or generate water. In addition, dimethoxymethane is stable, unlike other sources of formaldehyde which require water and methanol which then need to be taken into account in subsequent reaction and product separation. A further advantage of the present invention is the low level of decomposition in the present invention of dimethoxymethane to dimethylether and formaldehyde.

Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol:water in the ratio 30 to 60%:0.03 to 20%:35 to 60% by weight. Most preferably, by the term formalin is meant a mixture of formaldehyde:methanol:water in the ratio 35 to 55%:0.05 to 18%: 42 to 53% by weight.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

Preferably, the ethylenically unsaturated acid or ester produced by the process of the invention is selected from methacrylic acid, acrylic acid, methyl methacrylate, ethyl acrylate or butyl acrylate; more preferably, it is an ethylenically unsaturated ester, most preferably, methyl methacrylate.

The process of the invention is particularly suitable for the production of acrylic, alkacrylic, 2-butenoic, cyclohexenoic, maleic, itaconic and fumaric acids and their alkyl esters, and also methylene substituted lactones. Suitable, alkacrylic acids and their esters are ($C_{0-8}$alk)acrylic acid or alkyl ($C_{0-8}$alk)acrylates, typically from the reaction of the corresponding alkanoic acid or ester thereof with a methylene source such as formaldehyde in the presence of the catalyst, preferably the production of methacrylic acid or especially methyl methacrylate(MMA) from propanoic acid or methyl propionate respectively. Suitable methylene substituted lactones include 2-methylene valerolactone and 2-methylene butyrolactone from valerolactone and butyrolactone respectively.

The reaction of the present invention may be a batch or continuous reaction.

The term "alkyl" when used herein, means, unless otherwise specified, $C_1$ to $C_{12}$ alkyl and includes methyl, ethyl, ethenyl, propyl, propenyl butyl, butenyl, pentyl, pentenyl, hexyl, hexenyl and heptyl groups, preferably, the alkyl groups are selected from methyl, ethyl, propyl, butyl, pentyl and hexyl, more preferably, methyl. Unless otherwise specified, alkyl groups may, when there is a sufficient number of carbon atoms, be linear or branched, be cyclic, acyclic or part cyclic/acyclic, be unsubstituted, substituted or terminated by one or more substituents selected from halo, cyano, nitro, —$OR^{19}$, —$OC(O)R^{20}$, —$C(O)R^{21}$, —$C(O)OR^{22}$, —$NR^{23}R^{24}$, —$C(O)NR^{25}R^{26}$, —$SR^{29}$, —$C(O)SR^{30}$, —$C(S)NR^{27}R^{28}$, unsubstituted or substituted aryl, or unsubstituted or substituted Het, wherein $R^{19}$ to $R^{30}$ here and generally herein each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilcon groups, or mixtures thereof. Preferably, the alkyl groups are unsubstituted, preferably, linear and preferably, saturated.

The term "alkenyl" should be understood as "alkyl" above except at least one carbon carbon bond therein is unsaturated and accordingly the term relates to $C_2$ to $C_{12}$ alkenyl groups.

The term "alk" or the like should, in the absence of information to the contrary, be taken to be in accordance with the above definition of "alkyl" except "$C_0$ alk" means non-substituted with an alkyl.

The term "aryl" when used herein includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "halo" when used herein means a chloro, bromo, iodo or fluoro group, preferably, chloro or fluoro.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

Suitable optional alcohols for use in the catalysed reaction of the present invention may be selected from: a $C_1$-$C_{30}$ alkanol, including aryl alcohols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, phenol, n-butanol and chlorocapryl alcohol, especially, methanol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl) ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of substrate to be esterified. Thus the alcohol may serve as the reaction solvent as well, although, if desired, separate or further solvents may also be used.

Typical conditions of temperature and pressure in the process of the first aspect of the invention are between 100° C. and 400° C., more preferably, 200° C. and 375° C., most preferably, 300° C. and 360° C.; between 0.001 MPa and 1 MPa, more preferably, 0.03 MPa and 0.5 MPa, most preferably, between 0.03 MPa and 0.3 MPa. Typical residence times for the reactants in the presence of the catalyst are between 0.1 and 300 secs, more preferably, 1-100 secs, most preferably, 2-50 secs, especially, 3-30 secs.

Advantageously, use of the catalyst of the present invention has been found to produce remarkably low levels of unwanted side products in the reaction of formaldehyde or a suitable source thereof with a carboxylic acid or ester to produce an ethylenically unsaturated carboxylic acid or ester. In particular, remarkably low levels of dimethyl ether (DME) are produced compared to conventional catalysts such as aluminium phosphate. In addition, the catalysts provide excellent selectivity and activity.

The amount of catalyst used in the process of the present invention is not necessarily critical and will be determined by the practicalities of the process in which it is employed. However, the amount of catalyst will generally be chosen to effect the optimum selectivity and yield. Nevertheless, the skilled person will appreciate that the minimum amount of catalyst should be sufficient to bring about effective catalyst surface contact of the reactants during the contact time. In addition, the skilled person would appreciate that there would not really be an upper limit to the amount of catalyst relative to the reactants but that in practice this may be governed again by the contact time required and/or economic considerations.

The relative amount of reagents in the process of the invention can vary within wide limits but generally the mole ratio of formaldehyde or suitable source thereof to the carboxylic acid or ester is within the range of 20:1 to 1:20, more preferably, 5:1 to 1:15. The most preferred ratio will depend on the form of the formaldehyde and the ability of the catalyst to liberate formaldehyde from the formaldehydic species. Thus highly reactive formaldehydic substances where one or both of $R^{31}$ and $R^{32}$ in $R^{31}O$—$(CH_2$—$O)_iR^{32}$ is H require relatively low ratios, typically, in this case, the mole ratio of formaldehyde or suitable source thereof to the carboxylic acid or ester is within the range of 1:1 to 1:9. Where neither of $R^{31}$ and $R^{32}$ is H, as for instance in $CH_3O$—$CH_2$—$OCH_3$, or in trioxane higher ratios are most preferred, typically, 3:1 to 1:3.

As mentioned above, due to the source of formaldehyde, water may also be present in the reaction mixture. Depending on the source of formaldehyde, it may be necessary to remove some or all of the water therefrom prior to catalysis. Maintaining lower levels of water than that in the source of formaldehyde may be advantageous to the catalytic efficiency and/or subsequent purification of the products. Water at less than 10 mole % in the reactor is preferred, more preferably, less than 5 mole %, most preferably, less than 2 mole %.

The molar ratio of alcohol to the acid or ester is typically within the range 20:1 to 1:20, preferably 10:1 to 1:10, most preferably 5:1 to 1:5, for example 1:1. However the most preferred ratio will depend on the amount of water fed to the catalyst in the reactants plus the amount produced by the reaction, so that the preferred molar ratio of the alcohol to the total water in the reaction will be at least 1:1 and more preferably at least 3:1.

The reagents may be fed to the reactor independently or after prior mixing and the process of reaction may be continuous or batch. Preferably, however, a continuous process is used.

Typically, the reaction in the method of the invention takes place in the gas phase. Accordingly, suitable condensing equipment is generally required to condense the product stream after reaction has taken place. Similarly, a vaporiser may be used to bring the reactants up to temperature prior to the catalyst bed. Preferably the vaporiser acts at a temperature within +/−150° C. of the reaction conditions, more preferably within +/−100° C., most preferably within +/−75° C. of the reaction conditions.

Preferably, the barium phosphate whether crystalline or otherwise forms 50-100 wt % of the catalyst, more preferably, 55-100wt %, most preferably, 60-100wt %, especially, 70-100wt %, more especially, 75-100wt %, most especially, 80-100wt % of the catalyst. The balance of the catalyst is made up of impurities, binders or inert materials. Generally, the barium phosphate forms about 80-90% of the catalyst. Included in the definition of crystalline barium phosphate are metal deficient or phosphate deficient barium phosphate having the Ba:P ratios and habit defined herein.

When binder is used in the present invention it may form up to 50 wt % of the catalyst. Alternatively, the binder may be used in conjunction with a catalyst support to bind the catalyst to the support. In the latter case, the binder does not form part of the catalyst as such.

Suitable binders for the catalyst of the present invention will be known to those skilled in the art. Non-limiting examples of suitable binders include silica (including colloidal silica), silica-alumina, such as conventional silica-alumina, silica-coated alumina and alumina-coated silica, and alumina, such as (pseudo)boehmite, gibbsite, titania, titania-coated alumina, zirconia, cationic clays or anionic clays such as saponite, bentonite, kaolin, sepiolite or hydrotalcite or mixtures thereof. Preferred binders are silica, alumina and zirconia or mixtures thereof.

The barium phosphate particles can be embedded in the binder or vice versa. Generally, when used as part of the catalyst, the binder functions as an adhesive to hold the particles together. Preferably, the particles are homogeneously distributed within the binder or vice versa. The presence of the binder generally leads to an increase in mechanical strength of the final catalyst.

The typical average surface area of the barium phosphate catalyst is in the range 0.1-500 $m^2g^{-1}$, more preferably, 1-200 $m^2g^{-1}$, most preferably, 1-50 $m^2g^{-1}$ as measured by the B.E.T. multipoint method using a Micromeritics TriStar 3000 Surface Area and porosity Analyser. The reference material used for checking the instrument performance is a carbon black powder supplied by Micromeritics with a surface area of 30.6 $m^2/g$ (+/−0.75 $m^2/g$), part number 004-16833-00.

The typical average particle size of the catalyst particles is in the range 0.01-50 μm, more preferably, 0.05-20 μm, most preferably, 0.1-5 μm as measured by a Malvern Zetasizer Nano S using dynamic light scattering and using NIST standards.

If the material is porous, it is preferably mesoporous with an average pore size of between 2 and 50 nm. Pore size can be determined by mercury intrusion porosimetry using NIST standards.

The average pore volume of the catalyst particles may be less than 0.01 $cm^3/g$ but is generally in the range 0.01-5 $cm^3/g$ as measured by nitrogen adsorption. However, microporous catalysts are not the most preferred because they may inhibit movement of reagents through the catalyst and a more preferred average pore volume is between 0.02-1.2 $cm^3/g$ as measured by BET multipoint method using nitrogen adsorption according to ISO 15901-2:2006. The Micromeritics TriStar Surface Area and Porosity Analyser is used to determine pore volume as in the case of surface area measurements and the same standards are employed.

In the case of a non supported catalyst, the barium phosphate may be used directly in the form of catalyst particles either free flowing or together with a suitable binder to create a solid of the desired shape and/or size. The particles may be of any suitable size and therefore also in the form of powder, granules or beads either with or without binder. Typically, the catalyst is used in the form of a fixed bed and for this purpose may be used alone or on a support and in the latter case may include a suitable catalytic binder to bind it to the support.

As mentioned above, the catalyst may be used on a support. In this case, the barium phosphate catalyst may form a suitable surface coating on a suitable support for a catalyst.

For the purposes of the present invention, the support does not form part of the catalyst.

The barium phosphates of the present invention are either unsupported or supported on a suitable support, for example, alumina, silica, silicon nitride, silicon carbide, colloidal silica, titania, zirconia or aluminium phosphate.

It will be understood by the skilled person that a catalyst of the invention may be added to a support by any suitable means. The catalyst may be fixed, preferably by calcination, onto a suitable support after deposition of the compound onto the support using a suitable salt in a suitable solvent and subsequent drying of the surface coated support. Alternatively, the catalyst or suitable catalyst salt precursors may be co-precipitated with the support or suitable support precursors such as a silica sol from a suitable solvent. Preferably, an oxide support is used, more preferably, an oxide support as mentioned herein.

It is also possible to use the catalyst of the present invention in a mixture or admixture with another catalyst according to the present invention or otherwise with or without a suitable binder.

Generally, the barium phosphate of the present invention is a neutral molecule and therefore the negatively charged phosphate and hydrogen phosphate or pyrophosphate anions and any other non-metals balance the positively charged barium ions present.

The barium phosphate compound may be supported on a suitable support such as silica, silicon nitride, silicon carbide, colloidal silica, alumina, titania or aluminium phosphate. The support may or may not be an alkali metal doped support. If the support is alkali metal doped, the alkali metal doping agent may be selected from one or more of caesium, potassium, sodium, or lithium, preferably, caesium or potassium, more preferably, caesium. Alternatively, the barium phosphate may itself be doped with any one or more of the above mentioned doping metals.

Preferably, when a separate support for the catalyst of the first or second aspect is used, the weight ratio of catalyst:support is in the range 10:1 to 1:50, more preferably, 1:1 to 1:20, most preferably, 2:3 to 1:10.

BRIEF DESCRIPTION OF THE DRAWINGS

Embodiments of the invention will now be described with reference to the following non-limiting examples and figures and by way of illustration only in which.

EXAMLPES

Figure 1:
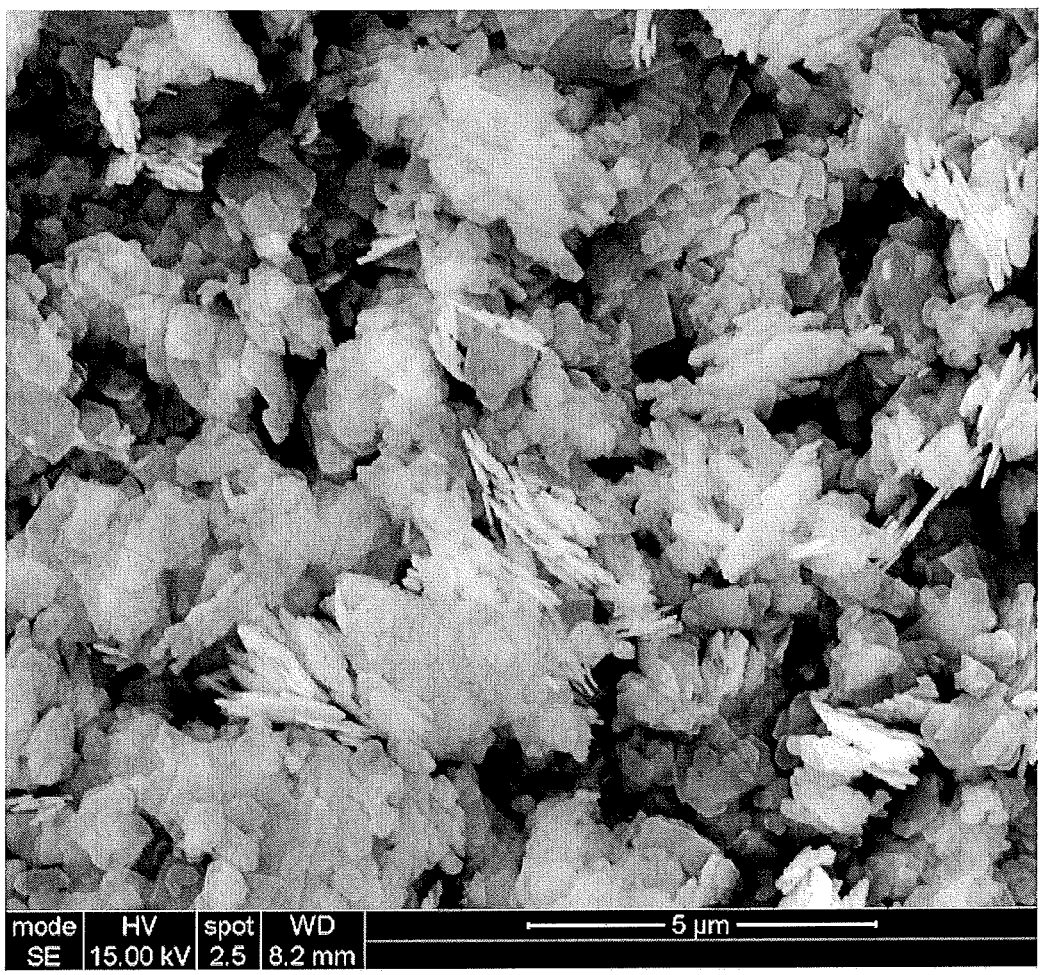
FIG. 1 shows a SEM Image of Example 1 crystals at the micrometer scale.
Figure 2:
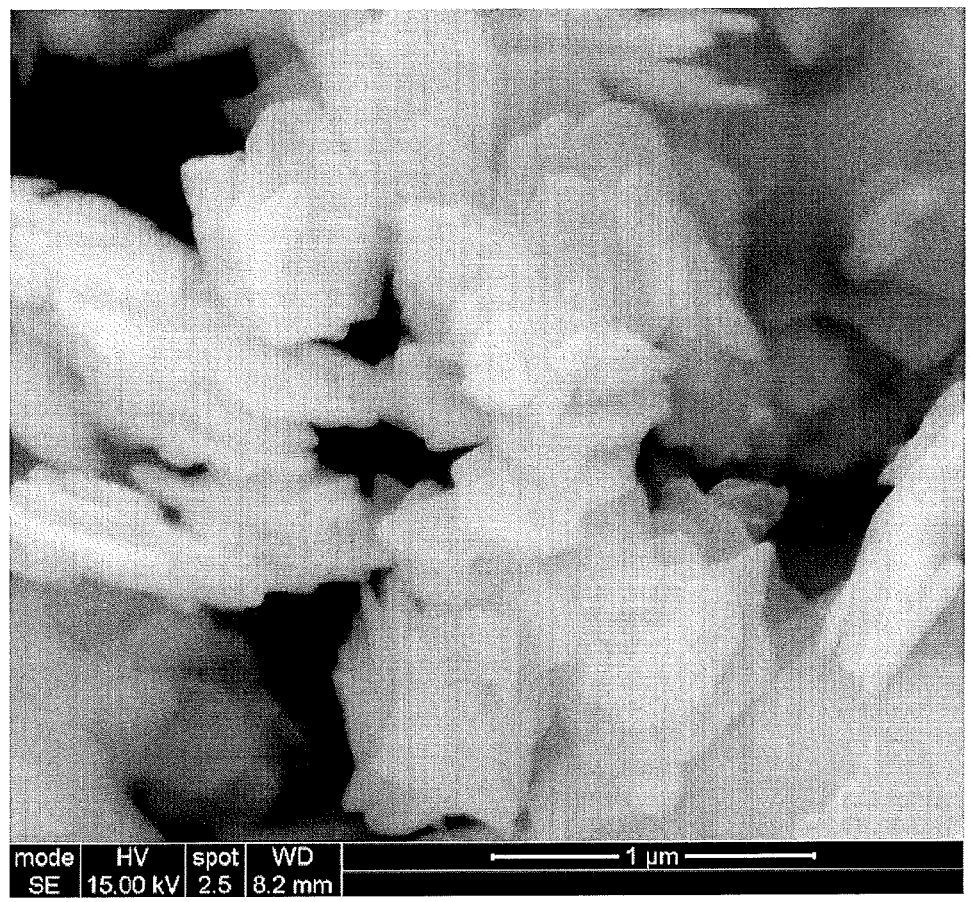
FIG. 2 shows a SEM Image of Example 1 crystals at the micrometer scale.
Figure 3:
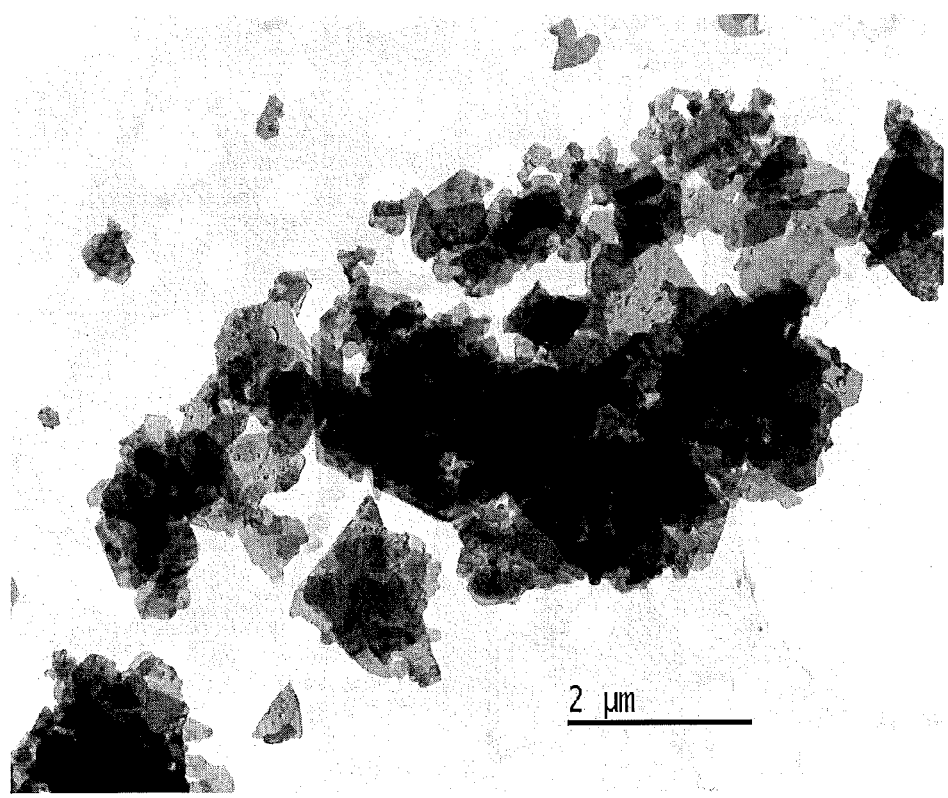
FIG. 3 shows a TEM Image of Example 1 crystals at the micrometer scale.
Figure 4:
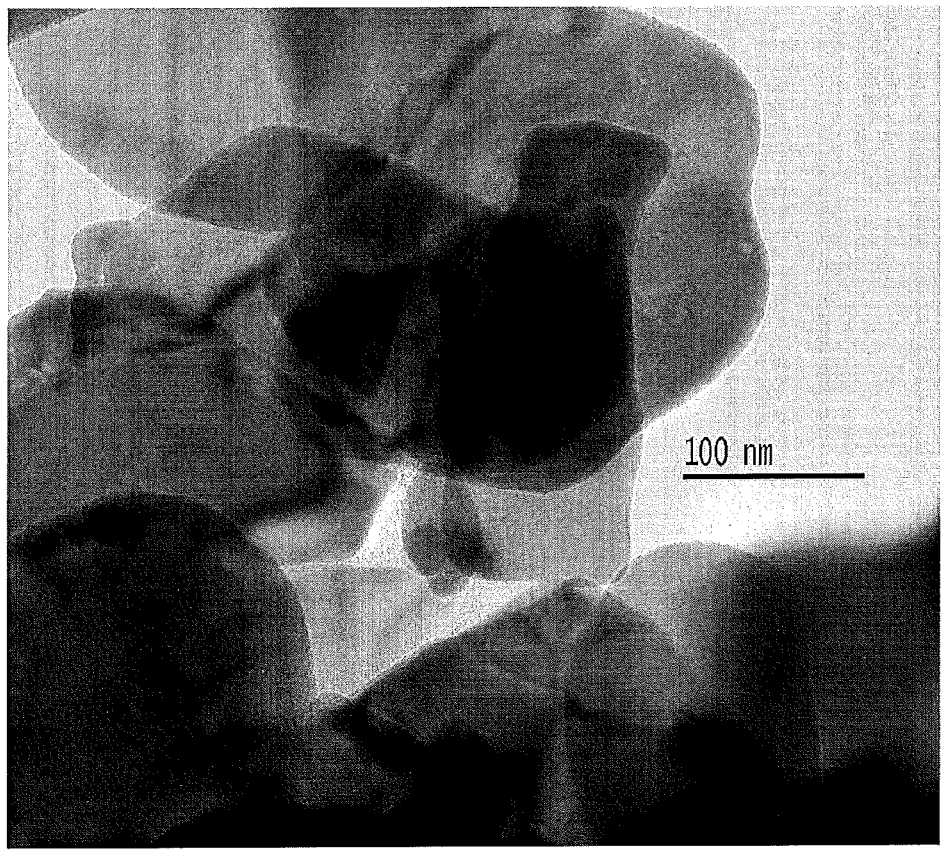
FIG. 4 shows a TEM Image of Example 1 crystals at the nanometer scale.
Figure 5:
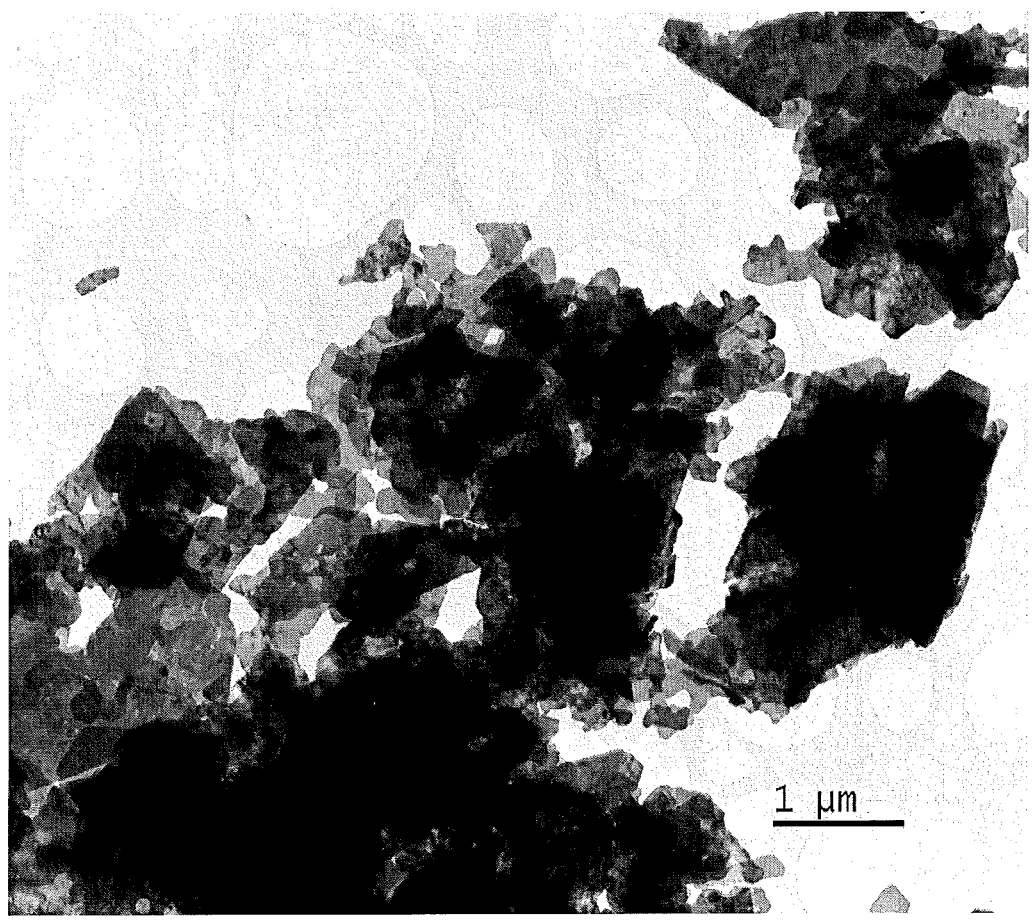
FIG. 5 shows a TEM Image of Example 2 crystals at the micrometer scale.
Figure 6:
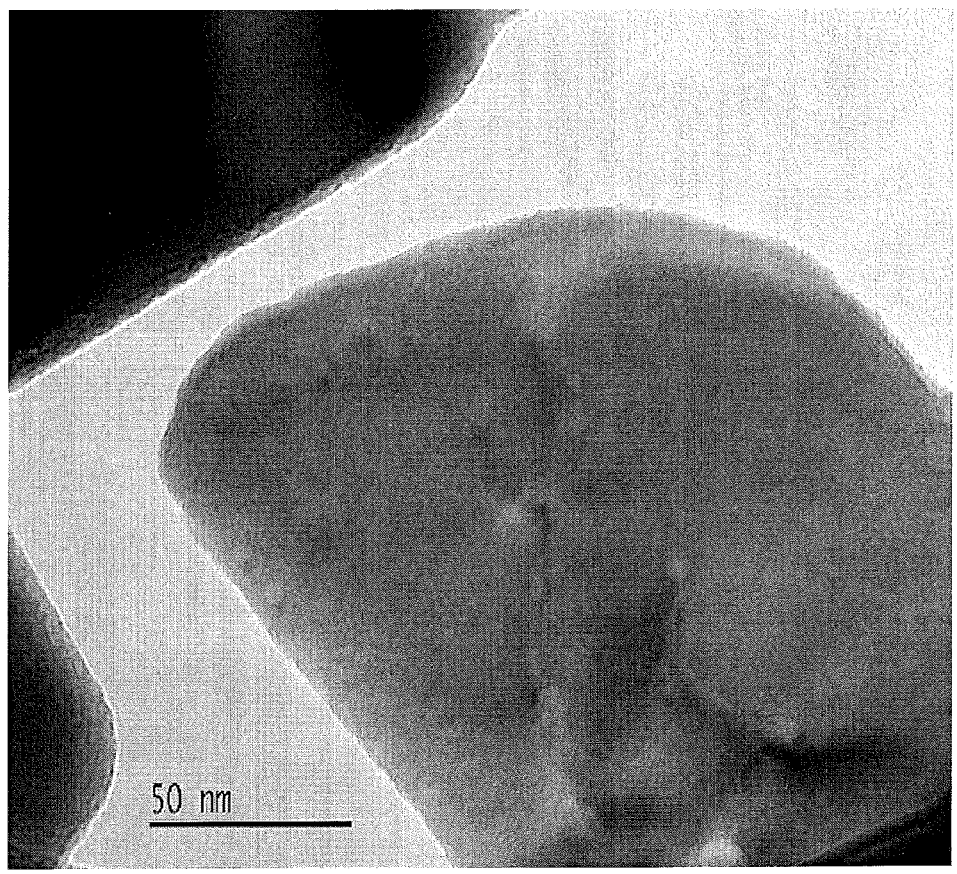
FIG. 6 shows a TEM image of Example 2 crystals at the nanometer scale.
Figure 7:
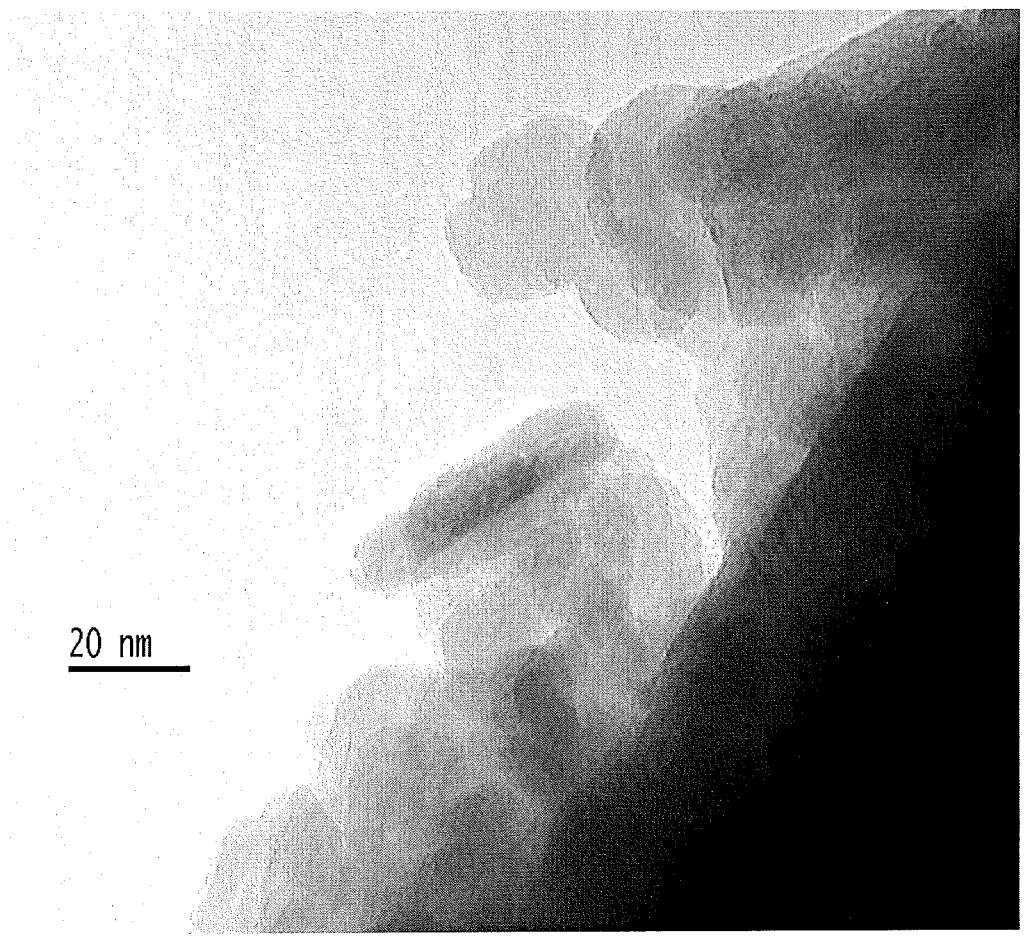
FIG. 7 shows a TEM image of Comparative Example 3 crystals at the nanometer scale.
Figure 8:
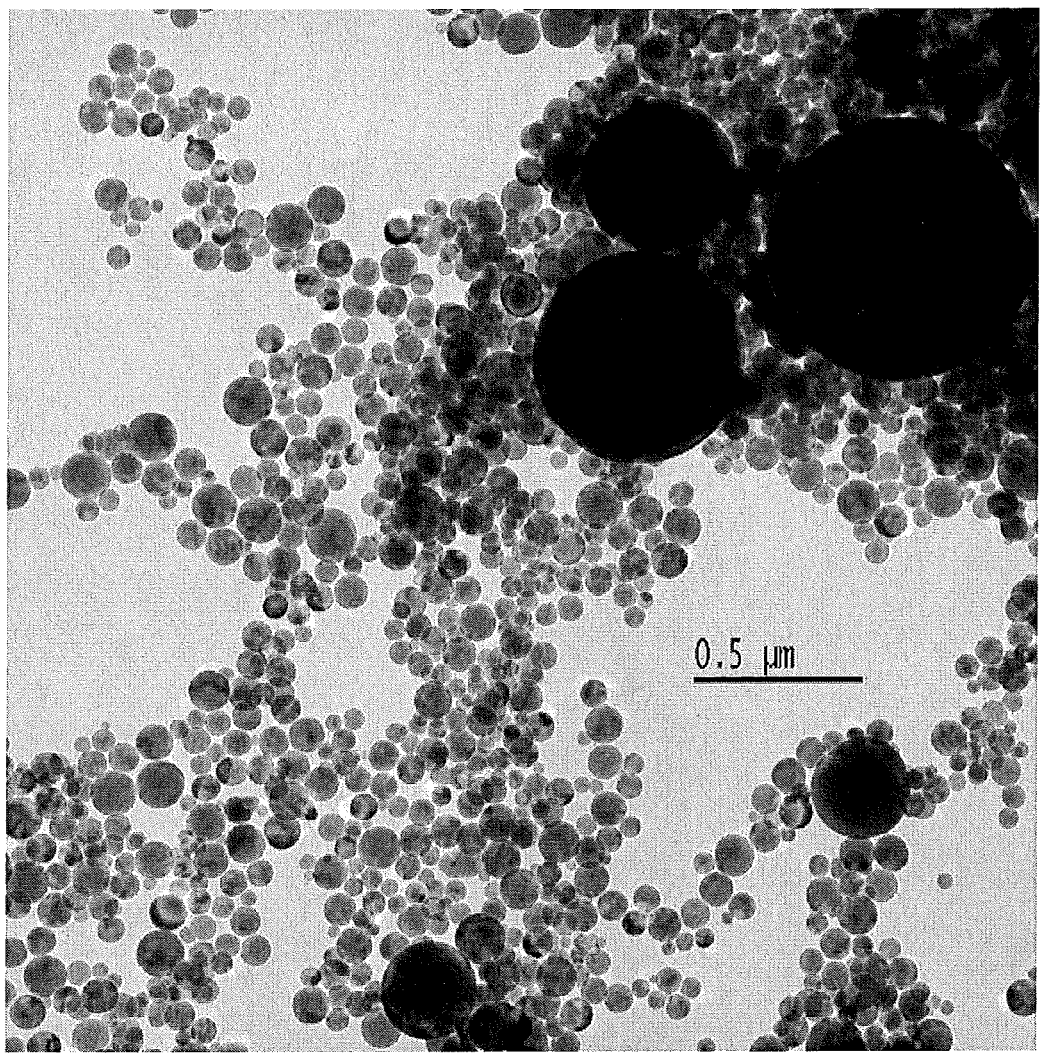
FIG. 8 shows a TEM image of Comparative Example 4 crystals at the nanometer scale.
Figure 9:
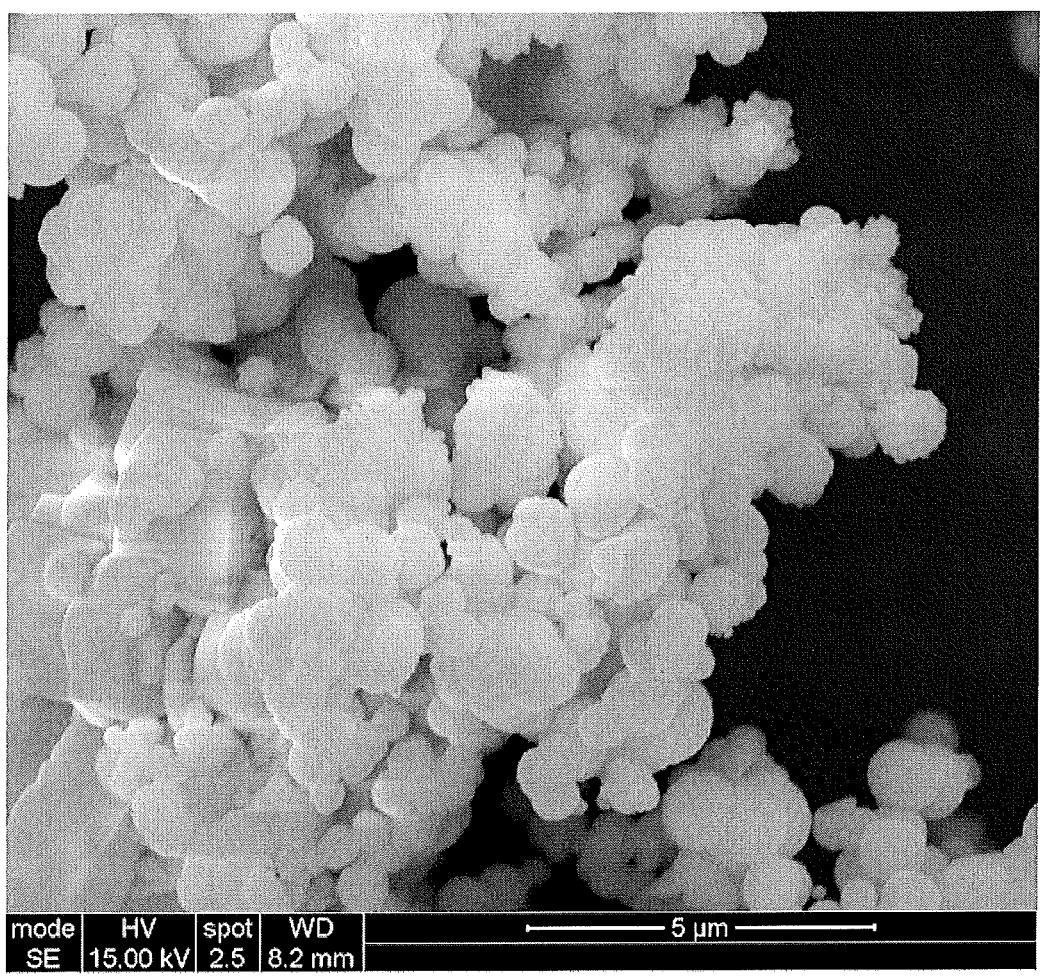
FIG. 9 shows a SEM Image of Comparative Example 5 crystals at the micrometer scale.

Experimental
Analytical Methods
XRD Experimental

The samples were prepared as dry compressed powder thin layer specimens mounted on single silicon crystal discs. The following instrument and settings were used.

| Instrument Siemens Bruker D5000 Diffractometer D6 | |
| --- | --- |
| X-ray Tube | Cu LFF |
| Radiation | Ca Kα |
| Generator Voltage | 40 kV |
| Generator Current | 40 mA |
| Diffraction Geometry | Reflection Bragg Brentano |
| Variable Divergence | Slit-12 mm irradiated length |
| Variable Antiscatter | Slit-12 mm irradiated length |
| Receiving Slit | 0.2 mm |
| Primary soller slit | 2.3° |
| Detector Si/Li Energy dispersive (monochromating) | |
| Monochromator | Detector (Kα) |
| Step Size | 0.02° |
| Time per step 3 seconds | ("$Sr_2P_2O_7$ pH7_1.67" = 6 seconds) |
| Scan start angle | 1.5 |
| Scan finish angle | 90 |
| Specimen format | Bulk |
| Specimen loading | Compressed powder on silicon discs |
| Specimen spinning | Yes |
| Temperature | Ambient |

Data output is in the form of a diffractogram, showing reflection intensity (counts per second) vs. angle 2θ°. Crystalline phase identification is carried out by comparison to reference ICDD (formerly JCPDS) diffractograms. Peak intensity or peak broadening analysis is performed to quantify morphological parameters for a crystalline phase.

XRF Experimental

Powder samples were ground and sieved to achieve particle size <100 μm (mesh). Approximately 1 gram of powder was lightly compacted into a primary sample cup with a thin film transmission base. The primary cup was held within the instrument by a secondary safety cup also with a thin film transmission base. The following instrument and conditions were used.

| Instrument Oxford Instruments X-Supreme 8000 (EDXRF) | |
| --- | --- |
| X-ray source | Tungsten |
| Source Energy | 6 keV |
| Tube Current | 10 μA |
| Chamber purge gas | Helium |
| Detector Silicon Drift proportional detector (SDD) | |
| Primary cup base | Poly4 film (4 μm thick) |
| Secondary cup base | Poly4 film (4 μm thick) |
| Specimen spinning | Yes |
| Temperature | Ambient |
| Repeat scans | 3 |

Ba Kα and P Kα fluorescence intensities (counts per second) were recorded. The ratio of peak intensities was converted to give a Ba:P ratio for the material, using a calibration scale obtained from the Ba Kα and P Kα signals for stoichiometric reference materials.

XPS Experimental

A microspatula of the powder sample was placed onto a piece of silicone-free tape attached to the instrument sample holder, and the loose powder gently flattened with the microspatula tip. The following instrument and settings were used.

| Instrument Kratos "Axis Ultra" X-ray Photoelectron Spectrometer | |
| --- | --- |
| X-ray source | Al Kα |
| Monochromator | Yes |
| Pass Energy- | 160 eV (survey scan), 40 eV & 10 eV (high-res scan) |
| Spot size | Ellipitic area, ~300 μm × ~700 μm. |
| Repeat scans | 2 |

Established Electron Spectroscopy for Chemical Analysis (ESCA) methods were utilised for qualification of the surface composition by elemental atomic percentage. Signal depth for oxide materials was ca. 3-5 nm, and the detection limit was about 1 atom in 1000 (i.e. 0.1 atom %, or 1000 ppm). Ba:P ratios were initially calculated from the experimental atomic percentages, and subsequently corrected for the presence of surface carbonaceous species.

TEM Experimental

Powder samples of the materials were suspended in water and drops were applied to copper grids bearing Lacey carbon support films. After drying, these were examined in a Philips CM12 TEM at an accelerating voltage of 120 kV.

Micrographs and electron diffraction patterns were collected at matching magnifications/tube-lengths. Selected regions were analysed using the associated NORAN Vantage EDX system. The variety of morphologies, compositions and crystalline species observed were recorded as images. The following instrument and settings were used.

| Instrument-Philips CM12 Transmission Electron Microscope | |
| --- | --- |
| Accelerating Voltage | 120 kV |

Two sets of experiments were run against various prepared examples of the invention and comparative examples. The first series of experiments were run using formaldehyde as a feed stream and the second series were run using dimethoxymethane as a feed stream. Analysis was carried out by gas chromatography, formaldehyde titration and with Karl Fischer apparatus. The analytical data were used to calculate the yield and selectivity of MMA+MAA. The selectivities in mole % relative to mole % MMA+MAA of diethylketone (DEK), dimethyl ether (DME) and toluene by-products are also tabulated in the catalyst test results below.

SEM experimental

Microgram quantities of powder samples were stub-mounted on carbon tabs, and platinum-sputtered to provide a very thin layer of conductive material. The mounted samples were examined in an FEI Quanta-250 FEG SEM system using conventional SEM mode (high vacuum, high voltage) over a range of accelerating voltages. Secondary electron micrographs showing topography were collected in 8-bit tif format.

TABLE 1

|  | Catalyst composition (Ba:P mole ratio) | pH/temp °C. | Contact time [s] | MMA + MAA yield [%] | MAA selectivity [mole %] | MMA + MAA selectivity [mole %] | DME [mole %] | DEK [mole %] | Toluene [mole %] |
|---|---|---|---|---|---|---|---|---|---|
| Ex 1 | BaPO (1.67) | 13/80 | 16.9 | 5.2 | 0.9 | 95.9 | 0.14 | 0.00033 | 0.00010 |
| Ex 2 | BaPO (1.67) | 11/80 | 9.7 | 3.4 | 0.4 | 95.8 | 0.07 | 0.00046 | 0.00011 |
| Ex 3 | BaPO (2.00) | 13/100 | 9.3 | 1.8 | 0.7 | 95.5 | 0.12 | 0.00029 | 0.00044 |
| Comp Ex 1 | AlPO_TiO_2_B_urea |  | 3.1 | 4.7 | 12.6 | 69.2 | 14.4 | 0.0609 | 0.00528 |
| Comp Ex 2 | AlPO |  | 1.5 | 4.8 | 12.9 | 78.0 | 10.6 | 0.0457 | 0.00446 |
| Comp Ex 3 | Ca-HAp 289396 |  | 7.0 | 0.2 | 0.1 | 72.3 | 0.2 | 0.0004 | 0.00005 |
| Comp ex 4 | Ca-HAp 677418 |  | 10.1 | 0.1 | 1.4 | 11.4 | 0.002 | 0.0025 | 0.00000 |
| Comp ex 5 | BaPO (1.00) | 8/50 | 11.1 | 0.2 | 0.0 | 87.1 | 0.04 | 0.00006 | 0.00003 |

Preparative Example 1

13.09 g of barium nitrate $Ba(NO_3)_2$ was dissolved in 200 ml of demineralised water and pH was adjusted to 13 with ammonium hydroxide. 3.96 g of diammonium hydrogen phosphate $(NH_4)_2HPO_4$ dissolved in 50 ml of demineralised water at pH 13 was added dropwise to the solution of barium nitrate at the temperature of 80° C. while stirring. A suspension forms on addition of the phosphate to the nitrate solution. This mother suspension was continuously stirred for 3 hrs after the dropwise addition was complete and pH was maintained at 13 with ammonium hydroxide throughout. After that the suspension was filtered and washed with demineralised water. Then it was dried at 110° C. overnight and calcined in air at 400° C. for 1 hr.

BET surface area of the material was 6.9 $m^2/g$. The sample was identified as a crystalline barium orthophosphate ($Ba_3(PO_4)_2$) type by XRD analysis. SEM images showed plate-like habit.

Catalyst testing: 3 g of catalyst as prepared in preparative example 1 was placed in a stainless steel tubular reactor connected to a vaporiser. The reactor was heated to 350° C. and vaporiser to 300° C. A mixture of 56.2 mole % of methyl propionate, 33.7 mole % of methanol, 9.6 mole % of formaldehyde and 0.5 mole % of water was passed through with the contact time indicated. The condensed reaction mixture was analysed by gas chromatography using a Shimadzu GC, equipped with a DB1701 column & a Flame Ionization Detector. For each analysis, the resultant chromatograph is processed using Shimadzu's GC solution software to obtain peak areas for individual components. FID response factors for the individual components are applied to convert peak areas, first into wt %, and then into mol %, of detectable material in the sample.

Selectivity with respect to MAA or MAA+MMA is calculated from the molar amount of the component produced (exit molar content, less feed molar content), as percentage of the molar amount of propionate converted to products.

Preparative Example 2

13.09 g of barium nitrate $Ba(NO_3)_2$ was dissolved in 200 ml of demineralised water and pH was adjusted to 11 with ammonium hydroxide. 3.96 g of diammonium hydrogen phosphate $(NH_4)_2HPO_4$ dissolved in 50 ml of demineralised water at pH 11 was added dropwise to the solution of barium nitrate at the temperature of 80° C. while stirring. A suspension forms on addition of the phosphate to the nitrate solution. This mother suspension was continuously stirred for 3 hrs after the dropwise addition was complete and pH was maintained at 11 with ammonium hydroxide throughout. After that the suspension was filtered and washed with demineralised water. Then it was dried at 110° C. overnight and calcined in air at 400° C. for 1 hr. BET surface area of the material was 12.6 $m^2/g$. The sample was identified as a crystalline barium orthophosphate ($Ba_3(PO_4)_2$) type by XRD analysis.

The preparative example 2 catalyst was tested as described in example 1.

Preparative Example 3

20.91 g of barium nitrate $Ba(NO_3)_2$ was dissolved in 200 ml of demineralised water and pH was adjusted to 13 with ammonium hydroxide. 5.28 g of diammonium hydrogen phosphate $(NH_4)_2HPO_4$ dissolved in 100 ml of demineralised water at pH 13 was added dropwise to the solution of barium nitrate at the temperature of 100° C. while stirring. A suspension forms on addition of the phosphate to the nitrate solution. This mother suspension was continuously stirred for 3 hrs after the dropwise addition was complete and pH was maintained at 13 with ammonium hydroxide throughout. After that the suspension was filtered and washed with demineralised water. Then it was dried at 110° C. overnight and calcined in air at 400° C. for 1 hr. BET surface area of the material was 7.0 $m^2/g$. The sample was identified as a crystalline barium orthophosphate ($Ba_3(PO_4)_2$) type by XRD analysis.

The preparative example 3 catalyst was tested as described in example 1.

Preparative Comparative Example 1

The catalyst was synthesised following the preparation method disclosed in U.S. Pat. No. 4,118,588 patent in Example 4.

3 g of titanium dioxide $TiO_2$ (Aldrich catalogue number 634662), 2.3 g of aluminium phosphate (prepared as in comparative example 2) and 0.75 g of boric acid $H_3BO_3$ were mixed together. A paste was produced by addition of 0.25 g of urea in 5 ml of demineralised water. The paste was dried for 2 hrs at 120° C. and then heated for 4 hrs at 600° C.

The catalyst was tested as described in example 1.

Preparative Comparative Example 2

37.5 g of aluminium nitrate nonahydrate $Al(NO_3)_3.9H_2O$ and 13.2 g of diammonium hydrogen phosphate $(NH_4)_2HPO_4$ were dissolved together in 160 ml of demineralised water acidified with nitric acid $HNO_3$. Solution of ammonium hydroxide was added until pH 7 was reached. Formed hydrogel was mixed for further 1 hr, after that it was filtered and washed with water. It was dried at 80° C. overnight and then calcined in air at 600° C. for 1 hr. BET surface area of the material was 181 $m^2/g$.

The catalyst was tested as described in example 1.

Preparative Comparative Example 3

Commercial Ca-hydroxyapatite was used from Aldrich with catalogue number of 289396. The sample was confirmed as a crystalline hydroxyapatite type by XRD analysis. Some amorphous material was found. TEM showed the presence of agglomerated irregular sphere like particles.

The catalyst was tested as described in example 1.

Preparative Comparative Example 4

Commercial Ca-hydroxyapatite was used from Aldrich with catalogue number of 677418. The sample was confirmed as crystalline hydroxyapatite type by XRD analysis. TEM showed evenly-shaped nano-spheres, typically 50-100nm diameter (although with some individual spheres of 300-800nm diameter), with no evidence of any non-spherical habit.

The catalyst was tested as described in example 1.

Preparative Comparative Example 5

13.07 g of barium nitrate $Ba(NO_3)_2$ was dissolved in 200 ml of demineralised water and added dropwise to 4.94 g of pyrophosphoric acid $H_4P_2O_7$ in 100 ml of demineralised water at 50° C. while stirring. The pH of solution was ten adjusted to 8 by dropwise addition of aqueous ammonia to obtain precipitate. The suspension was filtered and washed with demineralised water. Then it was dried at 110° C. overnight and calcined in air at 400° C. for 1 hr.

BET surface area of the material was 2.0 $m^2/g$. The major phase was identified by XRD as a crystalline barium pyrophosphate $(Ba_2P_2O_7)$. Barium hydrogenphosphate $(BaHPO_4)$ was found as a minor phase. SEM images showed spheres as a dominant morphology.

The preparative comparative example 5 catalyst was tested as described in example 1.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the preferred, typical or optional invention features disclosed in this specification (including any accompanying claims, abstract and drawings), or to any novel one, or any novel combination, of the preferred, typical or optional invention steps of any method or process so disclosed.

The invention claimed is:

1. A method of producing an ethylenically unsaturated carboxylic acid or ester, comprising the steps of
    contacting formaldehyde or a suitable source thereof with a carboxylic acid or ester in the presence of a catalyst and optionally in the presence of an alcohol,
    wherein the catalyst comprises barium phosphate leaf or plate shaped/like crystals.

2. The method according to claim 1, wherein the phosphate is selected from pyrophosphate, orthophosphate ($PO_4^{2-}$), hydrogenphosphate and mixtures thereof.

3. The method according to claim 1, wherein the catalyst is at least 50% w/w barium phosphate.

4. The method according to claim 1, wherein selectivity of the reaction to the ethylenically unsaturated carboxylic acid or ester is to an(alk)acrylic acid or alkyl (alk)acrylate product and is at least 40 mole %.

5. The method according to claim 1, wherein at least 10% mol/mol of the total barium phosphate in the catalyst is in a crystalline form.

6. The method according to claim 1, wherein the average crystal size of the barium phosphate crystals ranges from 0.002 µm to 50 µm.

7. The method according to claim 1, wherein the plates have an average thickness ranging from 0.002 µm to 2 µm.

8. The method according to claim 1, wherein doping elements are present in the catalyst at a level up to 20 mol % of a metal M within the catalyst.

9. The method according to claim 8, wherein the doping elements are cations selected from Cs, K, Rb, Na, Li, Zn, Ti, Si, Ln, Ce, Eu, Mg, Pb, Cd, Ag, Co, Cu, Ni, Sn, Ge, Hf and Zr.

10. The method according to claim 1, wherein doping anions are present in the catalyst at a level of up to 20 mol % phosphate.

11. The method according to claim 10, wherein the doping anions are selected from chloride and fluoride.

12. The method according to claim 1, wherein the carboxylic acid or ester reactant of the present invention is of formula R3-CH2-COOR4 wherein R4 is either hydrogen or an alkyl group and R3 is either hydrogen, an alkyl or aryl group.

13. The method according to claim 1, wherein a suitable source of formaldehyde is a compound of formula I

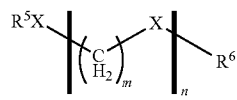

wherein R5 and R6 are independently selected from C1-C12 hydrocarbons or H,
X is O,
n is an integer from 1 to 100, and
m is 1.

14. The method according to claim 1, wherein the ethylenically unsaturated acid or ester produced by the process of the invention is selected from acrylic, alkacrylic, 2-butenoic, cyclohexenoic, maleic, itaconic and fumaric acids and their alkyl esters, and also methylene substituted lactones.

15. A catalyst system comprising a crystalline barium phosphate catalyst and optionally a catalyst support wherein the barium phosphate is in the form of leaf or plate shaped/like crystals.

16. The method according to claim 1, wherein the ethylenically unsaturated carboxylic acid or ester is α, β ethylenically unsaturated carboxylic acid or ester.

* * * * *